United States Patent
Herskovic et al.

(10) Patent No.: US 12,350,515 B1
(45) Date of Patent: Jul. 8, 2025

(54) VARIABLE VOLUME BRACHYTHERAPY STENT, METHOD FOR DELIVERING VARIABLE DOSIMETRIES IN BRACHYTHERAPY

(71) Applicants: Arnold M. Herskovic, Chicago, IL (US); Joshua Herskovic, Boca Raton, FL (US)

(72) Inventors: Arnold M. Herskovic, Chicago, IL (US); Joshua Herskovic, Boca Raton, FL (US)

( * ) Notice: Subject to any disclaimer, the term of this patent is extended or adjusted under 35 U.S.C. 154(b) by 0 days.

(21) Appl. No.: 18/785,498

(22) Filed: Jul. 26, 2024

(51) Int. Cl.
*A61N 5/10* (2006.01)

(52) U.S. Cl.
CPC .................. *A61N 5/1001* (2013.01)

(58) Field of Classification Search
CPC .......................................... A61N 5/1001–1029
See application file for complete search history.

(56) References Cited

U.S. PATENT DOCUMENTS

| | | | | |
|---|---|---|---|---|
| 2009/0209805 A1* | 8/2009 | Lubock | ................. | A61N 5/1015 600/7 |
| 2018/0339171 A1* | 11/2018 | Marsteller | ............. | A61N 5/1007 |
| 2020/0376294 A1* | 12/2020 | Herskovic | ............... | A61L 31/12 |

* cited by examiner

*Primary Examiner* — Thaddeus B Cox
(74) *Attorney, Agent, or Firm* — CHERSKOV FLAYNIK & GURDA

(57) ABSTRACT

A brachytherapy device is provided comprising a first conduit defining a first volume adapted to receive a radioactive fluid, a second conduit defining a second volume and frictionally engaged with the first conduit. Also provided is a method for varying the radiation dosage in vivo during brachytherapy treatment, the method comprising infinitely varying the volume of radiation exposed to the patient. This volume variation feature is utilized as clinically indicated and can further reduce the risk of slippage of the device in situ.

11 Claims, 4 Drawing Sheets

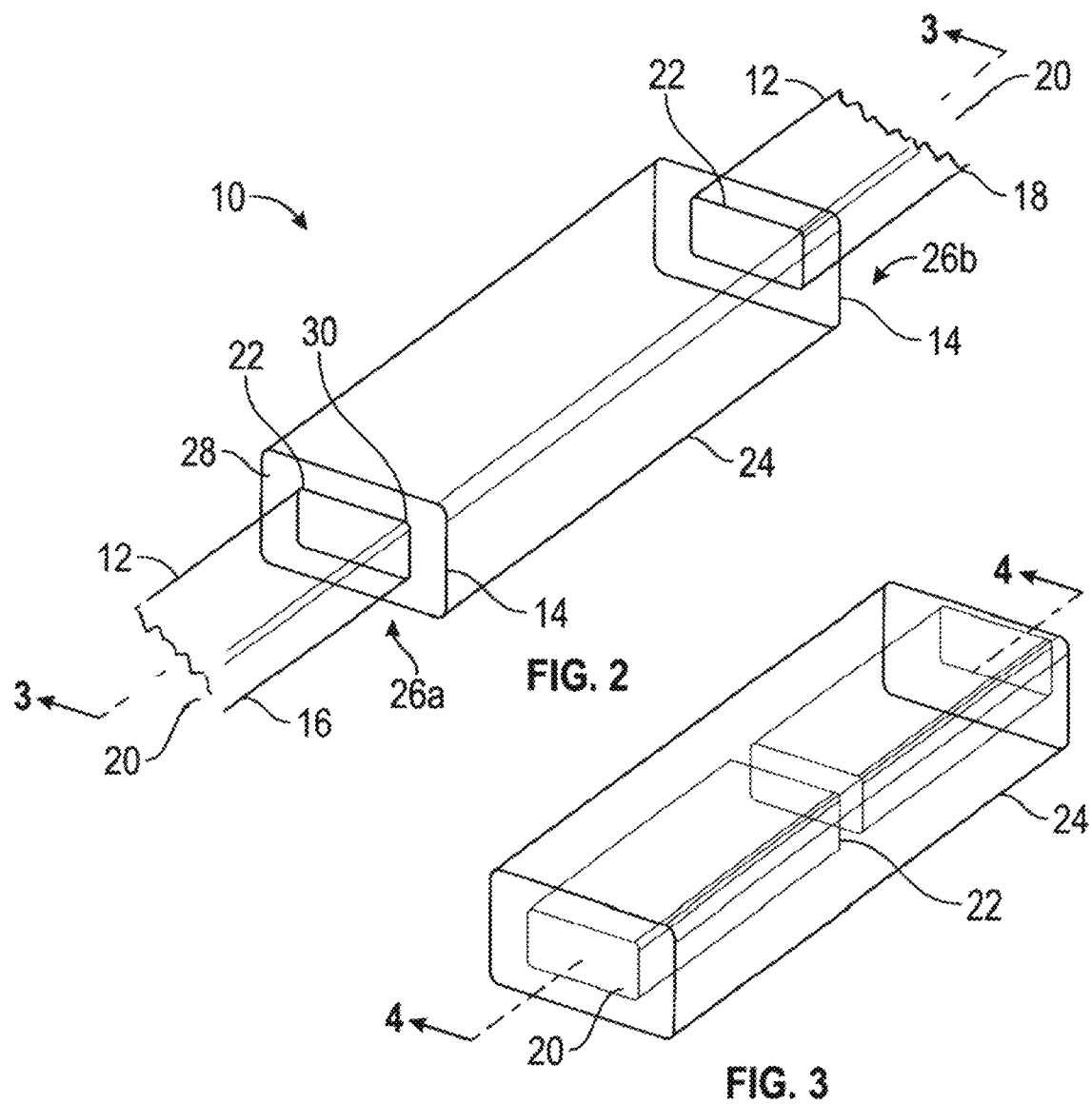

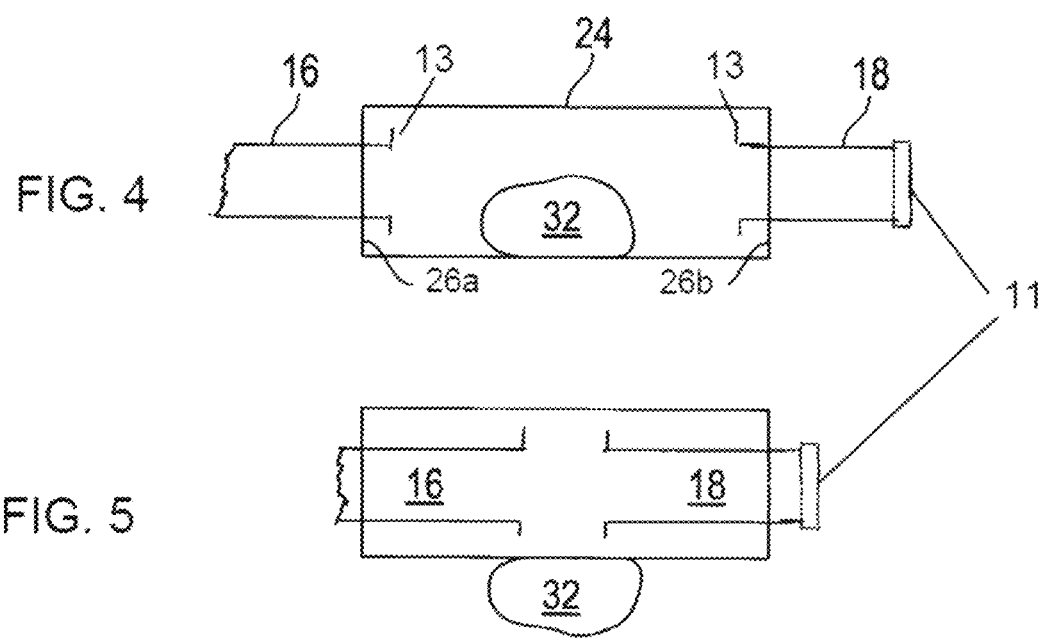

VARIABLE VOLUME BRACHYTHERAPY STENT, METHOD FOR DELIVERING VARIABLE DOSIMETRIES IN BRACHYTHERAPY

BACKGROUND OF THE INVENTION

1. Field of the Invention

This invention relates to a device and method for brachytherapy, and more specifically, this invention relates to a device and method for varying the radiation dose and radiation volume during brachytherapy treatments.

2. Background of the Invention

Brachytherapy features the use of radioactive sources placed in close proximity to tumor sites in efforts to eradicate the cancer associated therewith. An ongoing problem with brachytherapy and conventional radiotherapy is its potential for harming healthy tissue adjacent to the targeted diseased tissue.

A need exists in the art for a device and method for varying radiation exposure and volume during brachytherapy. The device and method should be easy to implement by personnel installing the brachytherapy stent into a patient. The device and method should also allow for reversibly adjusting the dose volume in vivo, which is to say after the device is implanted within a patient. The device and method should reproducibly deliver radiation doses in a potentially optimal manner such that only diseased tissue is exposed to medicament while healthy parenchyma is shielded from the medicament.

SUMMARY OF INVENTION

An object of the invention is to provide a brachytherapy device and method that overcomes many of the drawbacks of the prior art.

Another object of the invention is to provide a device and method for varying radiation volumes and total delivered dosages during brachytherapy. A feature of the invention is a first radio-isotope support structure (such as a first fluid space) overlaid by a second radio-isotope support structure (such as a second fluid space). An advantage of the invention is that simple manipulation of the device can vary either the total, or an integral of the total, radiation dose and volume to a tumor site.

Yet another object of the invention is to provide a device for varying brachytherapy volumes and dosages. A feature of the invention is that it is reversibly modified prior to or after implantation. An advantage of the invention is that the device allows for variation of dosage and volume to patient tissue without the need for changing the medicament, the medicament volume, or both, and even without the need for relocating the device within the patient. In many situations the dose is intended to be the constant and the medicament volume is reversibly adjusted to be clinically appropriate. The medicaments may be radioactive or non-radioactive in nature.

Still another object of the present invention is to provide a method for varying brachytherapy doses and volume in vivo and in situ. A feature of the invention is that it may be reversibly manipulated by medical personnel during or after implantation. An advantage of the invention is that this manipulation may be done remotely to the device without actually relocating the device, this to minimize further invasive activity leading to collateral damage. Alternatively, the device may change dimensions unaided by surgical personnel once inserted in tumor excised sites or tumor treatment sites. For example, the manipulation of the volume and dosage may occur spontaneously after implantation. These dimension changes may include changes to its length and cross sections (i.e., diameters) and may be induced by elastic, hydraulic and/or osmotic pressure, mechanical bias imposed by the shape memory constituents of the device, pH, body temperature and other physiological conditions. Alternatively, the dimension changes may be induced by shaped memory metals (e.g. nitinol), biocompatible foam or similar material and can provide the force to expand a spheroid (e.g., bladder shaped as a sphere, discussed below). Generally, the device provides a means to conformally fill a surgical defect or cancer/tumor excise site. Inasmuch as housing diameter changes may induce changes in housing length, housing constituents are selected to either maximize or minimize these length changes.

Briefly, a brachytherapy device is provided comprising a first longitudinally extending substrate (e.g., a rigid, semi-rigid or flexible solid or hollow rod, a solid or hollow ribbon, or a hollow conduit) defining a first medicament support surface. This medicament support surface is adapted to receive medicament either on the exterior or contained within the interior confines of the substrate (defining a first volume), or both on the exterior and in the interior of thereof. The medicament may be radioactive or nonradioactive, or a combination thereof.

The first longitudinally extending substrate may be defined by sequentially, and coaxially arranged shorter substrates. A plurality of housings defining a second medicament support surface or volume frictionally engage with the shorter substrates, akin to links in a chain. This frictional engagement may confine the shorter substrates to a specific length range that can be variable. If the medicament is radioactive, the housings may comprise radiation attenuating or filtering material. The housings may be leak proof so as to prevent leakage of fluid residing within the voids defined by the housings.

The housings may be attached to or integrally molded with a stent, the latter of which may have flared ends. These flared ends may accommodate physiological lumens (such as the GI tract which are dilated due to obstruction, but not necessarily associated with malignant tissues. These flared regions may be adapted to receive a several housings overlaying a single longitudinally extending substrate, the latter supporting or containing radioactive or non-radioactive fluid in the first volumes.

In an embodiment of the invention, several sequentially arranged first longitudinally extending substrates are overlaid by a plurality of housings and in slidable communication therewith. In this embodiment, the construct defines a first volume or surface in fluid communication with medicament. Some of the longitudinally extending exterior surfaces of that first volume are overlaid in with a plurality of housings. This entire construct forms an elongated structure. One or more of the elongated structures may be combined with an underlying foundation substrate such as a stent, with each of said devices loaded with similar portions of radiological material or different portions or radiological material, or some devices containing radiological material while other of the devices contained within the plurality contain non-radiological fluid or material.

Also provided is a method for varying the radiation dosage and/or volume in vivo to a patient during brachytherapy treatment, the method comprising infinitely varying the volume of radiation and the dose of radiation exposed to the patient.

BRIEF DESCRIPTION OF DRAWING

The invention together with the above and other objects and advantages will be best understood from the following detailed description of the preferred embodiment of the invention shown in the accompanying drawings, wherein:

FIG. 2 is an isometric view of a portion of a deployed brachytherapy device for in vivo manipulation of radiation dosage, in accordance with features of the present invention;

FIG. 3 is an isometric view of a portion of a nested brachytherapy device, in accordance with features of the present invention;

FIG. 4 is a view of FIG. 2 taken along lines 3-3;

FIG. 5 is a view of FIG. 3 taken along lines 4-4;

DETAILED DESCRIPTION OF THE INVENTION

The foregoing summary, as well as the following detailed description of certain embodiments of the present invention, will be better understood when read in conjunction with the appended drawings.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

The following detailed description should be read with reference to the drawings in which similar elements in different drawings are numbered the same. The drawings, which are not necessarily to scale, depict illustrative embodiments and are not intended to limit the scope of the invention.

As used herein, an element or step recited in the singular and preceded with the word "a" or "an" should be understood as not excluding plural said elements or steps, unless such exclusion is explicitly stated. As used in this specification and the appended claims, the term "or" is generally employed in its sense including "and/or" unless the content clearly dictates otherwise.

Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a method and device for varying the radiation dose and radiation volume during brachytherapy procedures. The invention accommodates different treatment diameters. Manipulations of the invented device may occur in situ after the device is implanted and a survey and/or calculation is made to determine dosage to the target tissue and collateral untargeted tissue. In one scenario, the entire implant is placed inside a patient and not further moved, but for extending portions of the device containing fluid isotope. However the brachytherapy device will reach the appropriate geometry relative to the physiological venue, such as the targeted lumen or post-operative surgical site and will optimize dose delivery to that venue. The invention does this via manual manipulation by medical personnel, or by the designed radial pressure imposed by its nitinol components, or by the inherent automatic extension of the device caused by the elasticity of radio-isotope reservoirs (e.g., balloons, discussed herein).

Device Overview

Figures 1A, 1B:
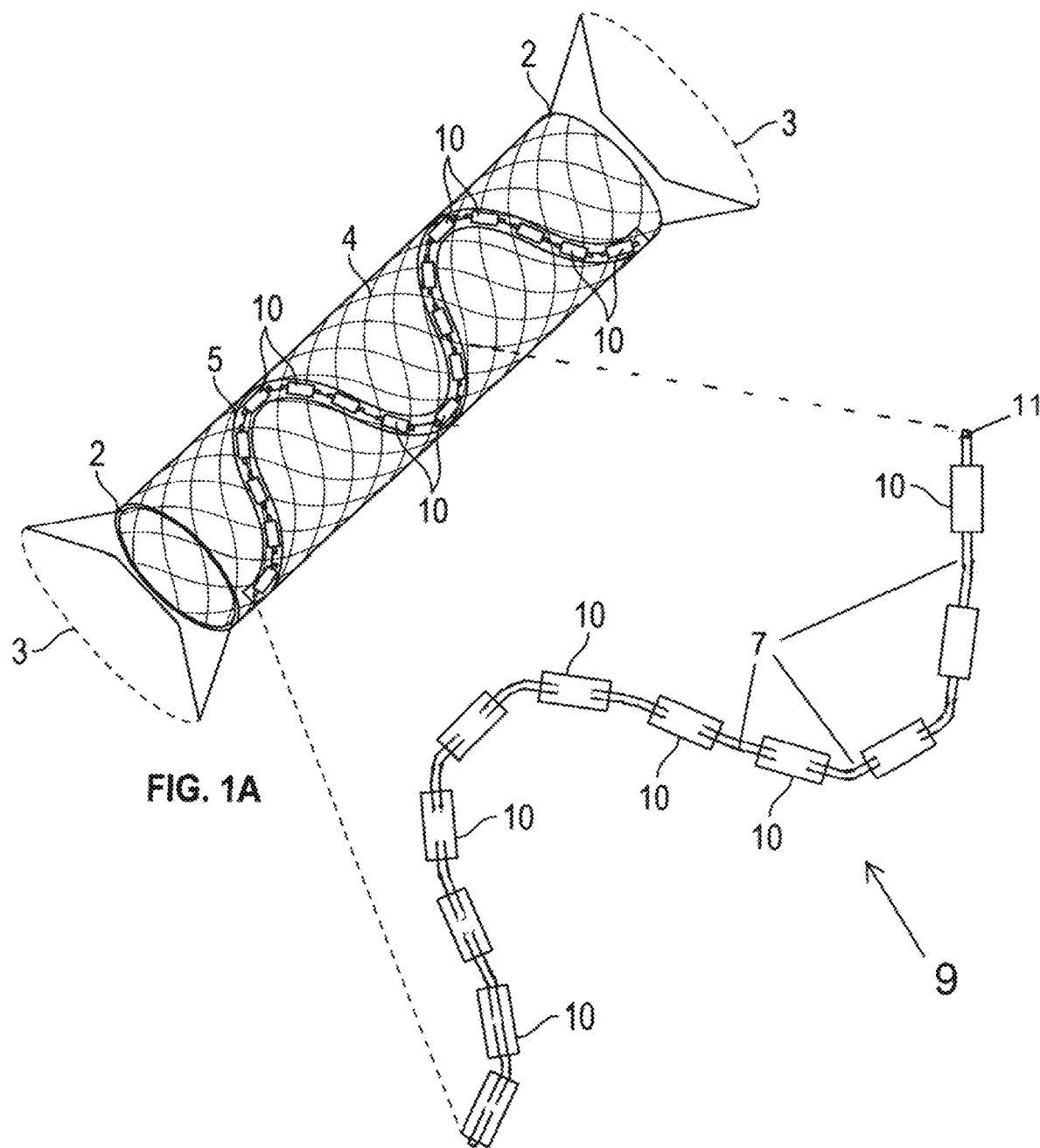
FIG. 1A is an overview of the device, in accordance with features of the present invention.
FIG. 1B is an exploded view of the invented device depicted in FIG. 1A, in accordance with features of the present invention.

Generally, the application of brachytherapy involves a stent 2 as depicted in FIG. 1A. The stent is generally shaped as a hollow cylinder and adapted to receive fluids (blood, beverages, bile, urine) and solids (food, feces, vomit) such that the fluids pass through the stent. The stent 2 is adapted to be positioned within physiological structures such as the esophagus, colon, ducts etc. For example, cylindrically shaped stents, may be adapted to receive fluids such that the fluids flow through the center of the stent. While the stent 2 is shown cylindrical in shape, other stents may be ovoid in shape, spherical in shape, planar in shape, or polyhedral in shape. Spherical- and/or ovoid-shaped stents may be adapted to be received by similarly shaped tumor excise sites such as are typical in breast or bladder surgeries.

The stent 2 as shown is designed to be slidably, and reversibly received by a physiological lumen such as the esophagus, trachea, bile duct, or even an artery. Ends 3 of the stent 2 may be flared to facilitate securement of the stent 2 within the lumen. The flares may be symmetrical so as to be the same shape, or asymmetrical so that one flare has a diameter different than the other. This asymmetry facilitates anchoring of the stent to physiological lumens similarly not symmetrical, or ravaged by tumors or rendered abnormal via natural anomalies. Further, the invented device (designated as numeral 9) may be incorporated into the flared ends 3 of the housing and may or may not contain radio-isotope.

The stent 2 usually comprises a biocompatible mesh 4 made of silicone, plastic, metal (such as nitinol), or other material and is generally flexible. The stent may have a cross section slightly smaller than the cross section opening of whatever physiological lumen slidably receives it.

Interior and/or exterior surfaces of the stent 2 may support a single longitudinally extending substrate 7, such as a rod, ribbon or conduit (the latter defining a hollow spiral structure 5), or several shorter longitudinally extending substrates 7 sequentially arranged, coaxially. Whether the longitudinally extending substrate 7 comprises a plurality of smaller substrates laid end to end or a single substrate, the two terminating ends of the resulting construct are sealed, as they should be to prevent medicament contained within the substrate from spilling therefrom. One such sealing means may be a cap 11, a crimp, a weld, or a combination thereof.

The substrate(s) may be shaped as the spiral 5 introduced supra. This spiral may be rigid, semi-rigid, or flexible. Exemplary constituents of this spiral a metal such as nitinol overlaid with a sealant. The spiral may define a variable diameter so as to accommodate varying diameter of the target tissues, those variations either naturally occurring (such as the GE junction) or due to an obstruction with secondary dilatation pre- or post-obstruction.

The sealant is applied so as to prevent leakage of fluid from the interior of the longitudinally extending substrate(s) 7 through the walls of the spiral. The longitudinally extending substrate(s) 7 is/are adapted to receive a fluid of radio-isotope, the fluid generally being a liquid or a gel. The gel may be an emulsion or a mixture of liquid and gaseous radio-isotopes, or even a suspension or colloidal fluid. Alternatively, exterior surfaces of the longitudinally extending substrate(s) 7 may support medicament (such as radio-isotope) that is overlaid with the aforementioned sealant so as to be hermetically sealed to the exterior support surfaces and therefore not in direct fluid communication with patient tissue.

The pitch or slant angle of any spiral is defined as the angle between the longitudinal axis (depicted in dashed line) of the stent and the longitudinal axis of a region of the longitudinally extending substrate 7. This angle may be adjusted to optimize swallowing function, duct fluid passage, or peristalsis within physiological lumens in which the device is inserted.

A section of the longitudinally extending substrate(s) 7 is depicted in FIG. 1B. That section depicts a plurality of housings positioned end to end along the longitudinally extending substrate(s). A module 10, a plurality of which comprise the device 9, is shown in greater detail in FIGS. 2-5.

The housing 24 may in part be radiation resistant so as to block any radiation from isotope contained within the aforementioned first volume that is overlaid by its respective housing. Alternatively, the housing 24 may be partly radiation resistant so as to block radiation of certain energies while letting other energies pass. The housing 24 may be radiation transmissive in some of its regions (for example in the middle of its construction or on a first patient-opposing surface) and partly radiation opaque or resistant in other regions (for example proximal to its ends 26a, 26b or on surfaces of the housing that do not directly oppose malignant parenchyma). These features allow implant personnel to juxtapose radiation transmissive housings to malignant tissues and juxtapose radiation resistant housings proximal to otherwise healthy tissue.

The housing 24 may be further comprised of biocompatible shape memory material such as polyurethane foams, such foams synthesized from symmetrical, low molecular weight and branched hydroxyl monomers. Such foams may be expanded or contracted on demand via external stimuli such as body heat, or ultraviolet light.

As shown in FIGS. 1A-1B there may be a plurality of housings 24 interacting with serially arranged (so as to be coaxial to each other) longitudinally extending substrates 7, the combination of which define a spiral. Ends 22 of each of the longitudinally extending substrates 7 which are overlaid by the housings may define a burr or flange 13, this to prevent complete pull out of the substrates 7 from their respective housing. As such the housings 24 are slidably arranged along the longitudinally extending substrates 7 reminiscent of railcars on a train. The housings each may be infinitely positioned (coaxially) along their respective substrate 7 to confer an infinite medicament dosage and/or volume to surrounding tissue.

FIGS. 1A-1B show the housings 24 extending from one end of the spiral to the other. However, there may be some instances where the housings 24 are localized in just one region of the stent. Alternatively, some of the devices 10 may contain radioactive fluid while other devices, perhaps along the same spiral 5, do not contain radioactive fluid. Further, the spiral may extend to the ends 3 of the stent, this to aid in keeping the stent in place, particularly when dealing with natural dilations of the lumen (e.g., the GE junction) or other natural artifacts perhaps caused by malignancies.

An embodiment of the device comprise a longitudinally extending substrate 7 that is solid (e.g., a rod or ribbon) and not hollow. Rather, exterior surfaces of the substrate 7 support radio-isotope, the radio-isotope applied to the exterior surfaces via adhesive, or as constituents in a film or paint applied to the exterior surfaces. The film or paint may be bio-compatible while simultaneously preventing separation of radio-isotope from the exterior surfaces, even as the substrate 7 is frictionally engaging with the housings 24. In this embodiment, the longitudinally extending substrate is a single piece.

In another embodiment, the device 10 comprises a plurality of longitudinally extending substrate(s) 7 serially arranged to define a hollow conduit 15 (thereby defining a first volume) with a first end 16 and a second end 18. The conduit 15 is adapted to slidably receive a plurality of housings 24. As such, linearly-extending portions of the conduit 15 are overlaid or otherwise contained with similarly arranged linearly positioned housings 24, such that each of those overlaid portions of the conduit define a first volume 12 adapted to receive a radioactive fluid. Each of the housings 24 define a second volume 14. The conduit may be configured as a straight line, or as a spiral, as shown.

The conduit 15 is frictionally engaged with the housings 24 and is generally radiation transparent. In an embodiment of the invention, the second volume is in fluid communication with the first volume. Generally, the first and second volumes are in radiological communication with each other, which is to say that the radiation energy of the first volume may be effected by the radiation energy of the second volume and vice versa.

Some of the housings 24 may be arranged along the hollow conduits 15 such that their ends 26a and 26b may contact the ends of adjacent housings. In this configuration, substantially most of the conduit 15 is overlaid by the housings such that very little of the conduit resides outside of the housing. This configuration may be employed when relatively smaller doses of radiation are required for treatment of tissue opposed to, or otherwise proximal to, the configuration. The left side of FIG. 1B depicts such an arrangement.

The right side of FIG. 1B depicts a configuration wherein the conduit is not nested or otherwise shielded or overlaid by housings. This configuration may be utilized in situations where patient tissue opposing the housings 10 require higher doses of radiation.

In addition, a plurality of parallel arranged spirals may be supported by the stent 2. Alternatively, the spiral may comprise a single device 10 which itself spirals circumferentially around the stent 2 so as to be supported thereby. In an embodiment of the invention, the modules 10 comprising the device 9 may be supported on an outside or external surface of the stent 2. In another embodiment, the device 9 may be supported on an interior surface of the stent such that the stent is positioned between physiological tissue (so as to actually contact the tissue), and the device 9.

The spiral 5 may comprise a hollow tube adapted to slidably receive several of the housings 24 such that the housings are arranged end to end. The tube may be fastened to an interior or exterior surface of the stent 2.

An embodiment of the invention provides a modular unit 10, each unit comprising a single housing 24 overlaying opposing ends of two hollow conduits. As discussed supra, a first volume 12 is defined by a first longitudinal section defining a portion of the hollow conduit 15 interacting with a single housing 24. The first and second ends of the first longitudinal section may be equally overlaid by their respective housing. Alternatively, one end of the first longitudinal section may be completely concealed for instance when an adjacent housing is positioned against the first housing, while the other end extends well outside the housing before frictionally engaging with a second adjacent housing. The housings 24 are adapted to move independently from each other but simultaneously axially controlled due to their frictional interaction with the hollow conduit 15 and the retaining burr 13. The modules are combined to form a single medicament delivery means, the means incorporating sequentially positioned conduits whose ends are all overlaid with housings.

The first longitudinal section and the second longitudinal section extend from the second volume 14 defined by the housing 24. In summary of this point, the housing 24 defines a larger cross section than do the conduits 16, 18. As such, the smaller hollow conduit(s) 16, 18, are adapted to slide in and out of the housing 24.

In a first position, the first longitudinal section 16 extends from a first end 26 of the housing 24 while the second longitudinal section 18 nests within the conduit so as to be overlaid by the housing 24. In this first position, the second volume is decreased to a third volume.

In a second position, the first and second longitudinal sections nest within the housing 24 so that both are overlaid by the housing 24. In this second position, the second volume is decreased to a fourth volume.

Method Overview

An objective of the invented method and device is to provide a uniform dose of medicament to target tissue. A device module 10 for varying the radiation volume and dosimetry in vivo during brachytherapy treatment is provided, the module comprising a first implantable housing adapted to receive radio-isotope fluid, wherein the housing comprises radiation attenuation material so as to be radiation resistant (such that no radiation penetrates the housing); a conduit in slidable communication with the first radiological space, wherein the conduit is wholly or partially radio-transparent; and extending or nesting the conduit within the housing, depending on radiation dosimetry required in the therapy. The conduit may be defined by a plurality of sequentially arranged longitudinally extending substrates such as rods, ribbons or hollow conduits. Each of the conduits may comprise two separate lumens (i.e., longitudinally extending portions) and each of the lumens comprise a distal end which resides outside of the housing and a proximal end which resides within the housing.

The lumens comprising the conduit are extended from the housing 24 (which also contains radioisotope) to expose patient tissue to a first radiation dose and volume and wherein the conduit is nested within the housing to expose patient tissue to a second radiation volume that is less than the first radiation volume. The conduit may be extended or nested in situ. Also, the conduit may be extended or nested remotely. Remote actuation occurs via an intentionally applied force selected from the group consisting of magnetization, electromagnetic force, palpation, pressure differentials and combinations thereof. Alternatively, deployment (i.e., axial extension) of the nested lumens outside of its housing may occur as a result of radial pressure experienced by the winding, wherein the winding comprises a shape memory material such as nitinol. Alternatively, the deployment of the conduit 5 from the housing 24 may occur automatically. For example, the nitinol could be in a spiral or linear shape and it could be programed to deliver radial pressure the planned elasticity of the balloon reservoir would force by pressure the extension of the effective nitinol ribbon.

The device 9 is configured such that the entire implant is placed inside a patient and not further moved, but for extending portions along the length of the device and at either end of the implant. The housing may be configured such that its cross section or length is increased to accommodate physiological widening which may exist naturally (e.g., the distal rectum, or the depending end of the esophagus distal to the gastroesophageal (GE) junction sphincter. Widening also occurs below or above an obstruction. This increase in the cross section of the housing may serve as an anchor even if there is no radioisotope included in parts thereof. This increase in cross section may actually be integrally formed with the body of the stent.

The radiation proof housing 24 may be reversibly flexible (e.g., reversibly expandable or contractible), when the housing is in fluid communication with a balloon such as a reversibly-deformable reservoir such as a bladder. In instances where the device 10 is encapsulated by a balloon, the balloon may reside between the housing 24 and patient tissue such that the balloon may oppose patient tissue and even contact patient tissue. In instances where radioactive fluid resides within the balloon, the balloon may need to be overlaid with radiation shielding material or radiation attenuation material, that material being as flexible or non-rigid as the balloon. Alternatively, the balloon is positioned within the stent so as not to contact the patient tissue.

The spiraled conduit (which is supported by the housing) expands radially when the contracting balloon increases internal fluid pressure within the device 10. This results in an increase in overall diameter or length of the device, but not necessarily an increase in radiation dose. Also, the method in which the spiral is made may result in an axial expansion of that spiral due to mechanical expansion or due to certain conditions related to pressure imposed by surrounding radio-isotopic fluid.

As depicted in FIG. 2, the device 10 comprises a first fluid space 12 (defining a first radiation volume) in slidable communication with a second fluid space 14 (defining a second radiation volume). In an embodiment, the spaces may be in fluid communication with each other. In another embodiment, the first radiation volume defined by the conduits 16, 18 are sealed such that no fluid communication occurs between the first and second fluid spaces.

The first fluid space (i.e., the first radiation volume) 12 may comprise two physically separate conduits 16 and 18, each of the conduits having a first distal end 20 and a second proximal end 22. The two proximal ends 22 may oppose each other from a distance, as depicted in FIG. 2 or in a relatively closer spatial relationship to each other, as depicted in FIG. 3, which shows the device in a nested configuration. The distal end 20 may actually reside inside of the adjacent housing 24 such that the conduits sequentially arranged form a single fluid passageway unbroken along the chain construct.

The first conduits 16, 18 are slidably received by the housing 24, the latter of which defines the second volume. As such, first and second ends 26 of the housing 24 comprise surfaces 28 forming apertures 30 having a cross section dimensioned to confer frictional interaction between the conduits 16, 18 and the housing apertures 30. As such, the apertures may be slightly larger than a second cross section defined by the conduits 16, 18. This frictional interaction between the housing 24 and the conduits 16, 18 prevents fluid leakage from the second housing to the patient. Additional elastic sealant may be applied to peripheries of the apertures 30 to prevent leakage and to compensate for slightly thinner dimensions (i.e., smaller cross sections) of the sliding conduits 16, 18.

FIG. 3 depicts the device in a nested configuration. In this configuration, the proximal ends of the first conduits 16, 18 are opposing each other so that the ends are in close spatial relationship. The conduits 16, 18 are shown coaxially aligned with each other and with the longitudinal axis of the housing 24 defining the second volume 14. However, in situations where an angle is associated with the tissue site to be treated, one of the conduits 16, 18 may enter the housing at an angle such that the one conduit is not coaxial with the other, or with the housing. In these situations, a top surface (upwardly facing) or bottom (downwardly facing) surface may define an aperture to slidably and frictionally receive that one non-coaxially arranged conduit.

FIGS. 3 and 4 are views taken along lines 3 and 4 of FIGS. 1 and 2 respectively. FIG. 4 shows the conduits 16 and 18 fully deployed so as to be substantially extended outside of the radio-opaque housing 24 and not shielded thereby. This configuration allows for maximum exposure of tissue to radiation embodied in isotopic fluids contained by, and flowing within, the conduits 16, 18. As discussed infra, the distal ends 20 and proximal ends 22 of the conduits 16, 18 may be sealed so the conduits 16, 18 combined with the housing 24 define the first and second fluid spaces, 12, 14. In this instance, the fluid spaces are not in fluid communication with each other.

The aforementioned reservoir (e.g. a bladder) defines a reversibly expandable third fluid space 32, as shown in FIGS. 3 and 4. The third fluid space 32 depicted in FIG. 4 is deflated, whereas it is shown as expanded in FIG. 5. Inasmuch as the third fluid space 32 is in fluid communication with the first and second fluid spaces in instances where the proximal ends 22 of the conduits are open, it's deflation in FIG. 4 is consistent with the fully deployed conduits 16, 18 not proximal to each other. The fully deployed conduits 16, 18 are not within the housing 24 to take up volume therein so that less pressure is imposed on the bladder. The bladder may be fully enclosed within the housing, or else reside outside of the housing. Preferably, the bladder is not interposed between the radioactive fluid and the target tissues.

When positioned within the second fluid space 14 as depicted in FIG. 4, the third fluid space 32 (so defined by the bladder) serves as a means to bias the conduits 16, 18 to a fully deployed position. When positioned outside of the fluid space 14, the third fluid space 32 services as a pressure differential means to bias the conduits 16, 18 to a fully nested position. The bladder 32 may be reversibly positioned inside or outside of the housing 24. Pressure differentials also may be imposed on the conduits 15 via inherently designed characteristics of the device, including radial pressure imposed by the nitinol metal.

Figure 6A:
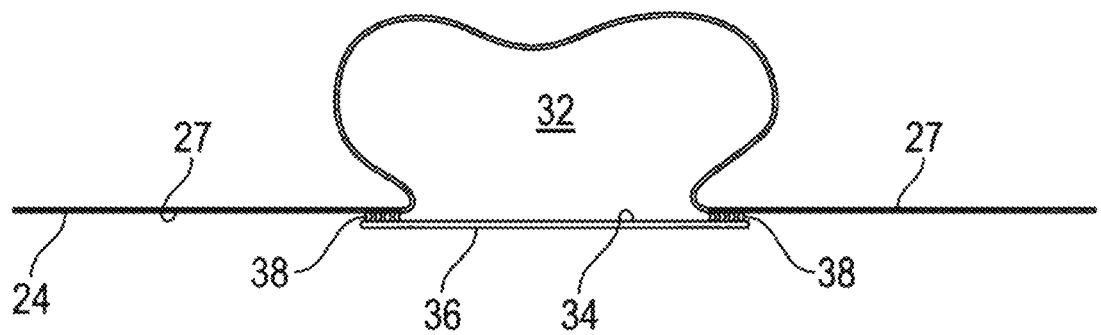
FIG. 6A shows a third radiation volume positioned within a housing of a brachytherapy vehicle, in accordance with features of the present invention.

FIG. 6A shows the bladder 32 residing within the housing 24. It should be appreciated that the housing may be cylindrical, ovoid, spherical, or polyhedral, as described supra. The bladder 32 is retained in the housing by a substrate 36 overlaying a periphery of a region of the housing 24 forming a bladder pass through aperture 34. The substrate 36 comprises radiation attenuating material and may be affixed to an exterior surface 25 of the housing 24 via a hook and pile fastener 38, or some other suitable fastening means. A mouth 33 of the bladder 32 may be hermetically sealed to either the exterior surface 25 of the housing, or a proximal interior surface 27 of the housing.

Figure 6B:
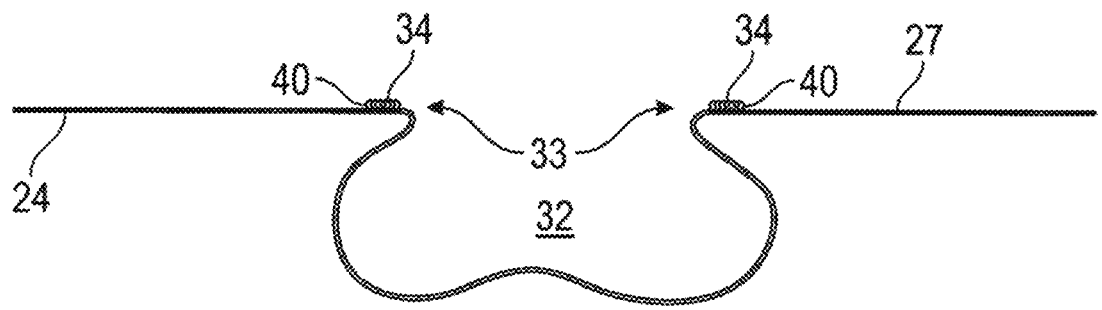
FIG. 6B shows a third radiation volume positioned outside a housing of a brachytherapy vehicle, in accordance with features of the present invention.

FIG. 6B shows the bladder 32 residing outside of the housing 24. In this view, the periphery defining the mouth 33 of the bladder is hermetically sealed to interior surfaces 27 of the housing 24 via adhesive 40.

The bladder (i.e. the third fluid space) 32 also provides additional space to contain extra radio-isotope fluid. The bladder may be overlaid with a radio opaque film or other material (such as high Z material) dispersed within an adhering polymer; this to prevent radiation from emanating from inside the bladder.

An intent of the bladder 32 is to provide a reasonably homogeneous dose of radiation to the device 10. For example, a spheroid-shaped stent 2 may be filed with radioactive fluid harbored within both the stent and the bladder, and given the contractual bias of the bladder, effect positive pressure of the stent 2 so as to cause the stent to expand.

Expansion of the spherical and/or ovoid-shaped stent may also be affected by filling the stent with a shape-memory foam which provides an outwardly directed force against internal surfaces of the stent.

Materials Detail

The conduits 16, 18 generally comprise relatively radio-transparent material selected from the group consisting of glass, plastic, ceramic, metal alloy (such as nitinol), and combinations thereof. Nitinol, which is a metal alloy of nickel and titanium, is a preferred material given its elasticity, fatigue resistance, and shape memory characteristics. The conduits 16, 18 may be solid in construction, thereby defining a fluid barrier between the lumen of the conduit and the exterior surface of the conduit. Alternatively, the conduits may comprise an underlying porous foundation akin to a slinky or spring to confer elasticity, reversible deformation characteristics and shape memory. That foundation in turn is overlaid with a sealant such as a polymer.

The housing 24 which slidably receives the conduits 16, 18 generally comprises radiation attenuating material selected from the group consisting of metals such as nitinol, polymers such as silicone, high Z material (such as materials containing the element(s) Ti or Cr or V or Fe or Pb or Bi) and others and combinations thereof. Alternatively, the housing may comprise radio-transparent material that is overlaid with radiation-resistant or radiation blocking/attenuating material such as high Z elements (e.g., bismuth) mixed with polymer such as silicone, other metal such as lead, and combinations thereof. The high Z material is to filter out undesirable radiation emanations.

The third fluid space 32 is generally elastic in nature so as to deflate and expand depending on the fluid pressure imposed on it by the two fluid spaces 12, 14. Suitable reversibly deformable materials include silicone balloons, rubber balloons, other flexible polymers, such as latex, polychloroprene, metalized plastic or a nylon fabric, and combinations thereof. Inasmuch as these elastic substrates are adapted to at least temporarily contain radioactive isotope-containing fluids, the substrates would be overlaid with a radio-opaque film, the film comprising high Z materials discussed supra.

The third fluid space 32 would define an opening so as to confer fluid communication with the second fluid space 14.

The periphery of the opening would be adhesively sealed to a portion of the housing defining a fluid ingress-egress point (such as an aperture) into and out of the housing. In an embodiment, the third fluid space 32 resides outside of the housing 24, particularly when subjected to positive pressure, as depicted in FIG. 5. In another embodiment, the third fluid space always resides within the housing.

The bladder may provide a means for remotely actuating the slidable conduits (and the first volume defined thereby) by means of pressure differential. That pressure differential may be applied from outside of the patient, or within the patient. In the second instance, the reversibly deformable bladder provides a means for biasing the conduits to either a deployed position, or a nested position.

As discussed supra, in one embodiment of the device, the conduits 16, 18 are loaded with radio-isotope and the conduits are sealed to prevent leakage therefrom. The conduits are then inserted or otherwise loaded within the housing 24 in a friction fit arrangement so as to prevent leakage of fluid (dwelling within the second fluid space 14) to outside of the housing.

In another embodiment, only the distal ends 20 of the conduits 16, 18 are sealed while the proximal ends 22 (i.e., those opposing each other remain unsealed. This confers fluid communication between the first and second volume. When the conduits are fully deployed from the housing, the surrounding parenchyma is expose to a larger volume of radiation. When the conduits are less than fully deployed from the housing such that a portion of the conduits are overlaid by the radiation-blocking housing, the surrounding parenchyma is exposed to a relatively smaller volume of radiation.

After assembly, the resulting construct is inserted into the patient, particularly at a tumor excise site or tumor site. Depending on the malady and the dosage required, the conduits 16, 18 are either deployed from inside the housing or partially left within the housing by the surgeon.

The conduits may extended or nested remotely. Remote actuation occurs via a bias selected from the group consisting of magnetization, electromagnetic force, palpation, pressure differentials and combinations thereof.

In operation, the invention varies the radiation dosage and volume in vivo during brachytherapy treatment by providing a first implantable housing adapted to receive radio-isotope fluid, wherein the housing is radiation impermeable or otherwise is constructed from radiation attenuating/filtering material to remove or minimize undesirable radiations. A longitudinally extending substrate, such as a solid rod or conduit in slidable communication with the first radiological (and physical) space is provided. If the longitudinally extending substrate is a rod, it is adapted to carry radioisotope on its surface (so as to be hermetically sealed on the surface). If the longitudinally extending substrate is a conduit, the conduit reversibly receives fluid containing radio-isotopes. The conduit is radio-transparent; and extends or nests within the housing, depending on radiation dosages required in the therapy.

Inasmuch as the conduit is in frictional engagement with the housing, the conduit may be nested or deployed anywhere along its longitudinally extending surfaces in contact with the housing. As such, the conduit positioning may be infinite (i.e., unlimited) along its longitudinally extending surface.

Turning back to FIG. 1B, a plurality of devices 9, each comprising a plurality of modules 10, may be arranged as a spiral extending along the surface of a stent 2. The surface supporting the devices 9 may be an external surface of the stent or an internal surface of the stent. In the system shown in FIG. 1B, the spiral is extending around the circumference of the stent Some of the devices 10 positioned near the ends of the stent are shown with their first and second conduits 14, 16 fully nested This nested configuration may be chosen to minimize radiation exposure to healthy tissue situated proximal to flared portions 3 of the stent.

Alternatively, devices 10 more medially situated on the stent 2 may have their first and second conduits 14, 16 deployed or otherwise extended from their housings 24. This configuration provides relatively greater radiation dose to tissue proximal to medial portions of the stent 2 that may require such treatment.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. For example, the differences in cross sectional dimensions are exaggerated in the drawings but it is expected that the dimensions will be as similar as practical. In addition, the attenuation of the radiation exposure in the walls of the housing may be adjusted in order to deliver a uniform dose. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all sub-ratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The invention claimed is:

1. A brachytherapy device comprising:
   a) a first conduit defining a first volume adapted to receive a radioactive fluid; and
   b) a housing defining a second volume frictionally engaged with the first conduit, wherein the housing comprises radiation attenuating or filtering material, wherein the second volume is in fluid communication with the first volume.

2. The device as recited in claim 1 wherein the first conduit comprises a first longitudinal section and a second longitudinal section coaxial with the first longitudinal section, wherein the first and second longitudinal sections are adapted to move independently from each other.

3. The device as recited in claim 2 wherein the first longitudinal section and the second longitudinal section extend from the housing.

4. The device as recited in claim 2 wherein the first longitudinal section extends from the housing while the second longitudinal section nests within the housing so as to be overlaid by the housing.

5. The device as recited in claim 2 wherein the first and second longitudinal sections nest within the housing so as to be overlaid by the housing.

6. The device as recited in claim 1 wherein the first conduit comprises a radio-transparent reversibly deformable material selected from the group consisting of metal, polymer, fiberglass, plastic, and combinations thereof.

7. The device as recited in claim 1 wherein the first conduit is nitinol and the first conduit is coated with a fluid impermeable substance.

8. The device as recited in claim 1 wherein the device is supported by a hollow stent having a shape selected from the group consisting of a cylinder, a sphere, an ovoid, a polyhedron and a plank.

9. A brachytherapy device comprising:
   a) a first conduit defining a first volume adapted to receive a radioactive fluid; and
   b) a housing defining a second volume frictionally engaged with the first conduit, wherein the housing comprises radiation attenuating or filtering material, the device further comprising a third volume in fluid communication with the first and second volumes.

10. The device as recited in claim 9 wherein the third volume is enclosed by the housing.

11. The device as recited in claim 9 wherein the third volume is positioned external of the housing.

* * * * *